(12) United States Patent
Burke et al.

(10) Patent No.: US 6,991,595 B2
(45) Date of Patent: Jan. 31, 2006

(54) ADAPTIVE SPEED CONTROL FOR BLOOD PUMP

(75) Inventors: David J. Burke, Concord, MA (US); Douglas C. Thomas, Carmichael, CA (US)

(73) Assignee: Thoratec Corporation, Pleasanton, CA (US)

( * ) Notice: Subject to any disclaimer, the term of this patent is extended or adjusted under 35 U.S.C. 154(b) by 329 days.

(21) Appl. No.: 10/125,943

(22) Filed: Apr. 19, 2002

(65) Prior Publication Data

US 2003/0199727 A1 Oct. 23, 2003

(51) Int. Cl.
*A61M 1/12* (2006.01)

(52) U.S. Cl. .......................... 600/17; 623/3.28
(58) Field of Classification Search ............ 600/16–17; 623/3.1, 3.28
See application file for complete search history.

(56) References Cited

U.S. PATENT DOCUMENTS

| | | | |
|---|---|---|---|
| 5,888,242 A | 3/1999 | Antaki et al. | |
| 6,066,086 A | 5/2000 | Antaki et al. | |
| 6,080,133 A | 6/2000 | Wampler | |
| 6,183,412 B1 | 2/2001 | Benkowski et al. | |
| 6,201,329 B1 | 3/2001 | Chen | |
| 6,234,772 B1 | 5/2001 | Wampler et al. | |
| 6,244,835 B1 | 6/2001 | Antaki et al. | |
| 6,342,071 B1 | 1/2002 | Pless | |
| 6,344,022 B1 | 2/2002 | Jarvik | |
| 6,572,530 B1 * | 6/2003 | Araki et al. | 600/17 |

FOREIGN PATENT DOCUMENTS

WO     WO 01/72352     10/2001

* cited by examiner

*Primary Examiner*—Robert E. Pezzuto
*Assistant Examiner*—Kristen Mullen
(74) *Attorney, Agent, or Firm*—Fish & Richardson P.C., P.A.

(57) ABSTRACT

A blood pump may be adapted to sense the onset of left ventricular collapse by monitoring a pulsatility index, and may adjust the pump speed to maintain the index at a setpoint. The pulsatility index may be measured by the amount of difference between the maximum and the minimum volume of flow through the pump during a particular time period. The setpoint may be increased when the onset of ventricular collapse is detected, for example, when the pulsatility index falls suddenly. The setpoint may be decreased incrementally when the onset of ventricular collapse has not been detected for a period of time, such as for a particular period of time since the last detection of the onset of ventricular collapse.

17 Claims, 3 Drawing Sheets

ADAPTIVE SPEED CONTROL FOR BLOOD PUMP

TECHNICAL FIELD

This application pertains to a blood pump. More specifically, the application relates to an apparatus and method for controlling the speed of an implantable blood pump so as to prevent left ventricular collapse.

BACKGROUND

The human heart is a pump—a complex and critical pump. As with any pump, the heart can become clogged and wear out over time. When wear and damage to the heart become sufficiently serious, the owner of the heart is said to have suffered severe heart failure. In such a situation, it is often necessary for the person to receive mechanical assistance for the heart or to receive a heart transplant. Where the person receives a transplant, mechanical assistance may still be needed until a donor heart is available.

Blood pumps are commonly used to provide mechanical assistance to the left ventricle of the heart. The left ventricle pushes blood out through the aorta and into the person's body. The left ventricle bears about eighty percent of the heart's load, and therefore is generally the first part of the heart to require assistance.

Ventricular assistance may be provided by a pump that is implanted in a person's abdomen, and that is connected in parallel with the person's cardiovascular system. In particular, an inflow conduit for a pump may be attached to the tip of the left ventricle, and an outflow conduit may be attached to the wall of the aorta. In this manner, some blood may take its normal route out of the ventricle and into the aorta, and other blood may pass through the pump, receive a boost, and be pushed into the body via the aorta.

The speed of the pump, and in turn the level of assistance provided by the pump, generally must be carefully controlled. The pump should be able to adapt to changes in demand for blood. For example, when a person exercises or is otherwise stressed, the pump generally must run faster to ensure that the heart provides adequate blood to the body. In adapting to changes in blood demand, the pump cannot run so slowly that blood does not get out of the heart and into the body. Similarly, the pump should not run so fast that it causes suction in the left ventricle. When suction occurs, the assist pump receives less blood flow, and the contractile properties of the ventricle may be adversely affected as the ventricle begins to collapse. Nonetheless, a rotary pump is generally most effective when it is running at the upper end of its range, which may be near the speed that causes ventricular collapse. Thus, it is important that a suction event that signifies the onset of ventricular collapse be sensed so that the pump may operate at an optimum speed.

It is possible to use sensors external to a blood pump, such as pressure transducers, to measure the flow rate and pressure through a pump, so that the pump's speed may be adjusted to compensate for changes in blood requirements. However, external sensors add complexity to a blood pump system, and also add complexity to the surgical procedure used to implant the system. In addition, sensors are generally encapsulated or coated with biological materials, which can render them unfit for long-term use.

Blood pumps may also sense or detect the activity of the heart indirectly by monitoring the blood flow through the pump, such as by measuring the current draw and speed of the pump over time. Such monitored variables may then be used to compute a revised speed for the pump, such as when ventricular suction is detected. Several such methods for adjusting the speed of an implantable blood pump are disclosed in U.S. Pat. Nos. 5,888,242 and 6,066,086. For example, cyclical current fluctuations of the pump during systole-diastole may be monitored for a detectable current spike that is indicative of the onset of ventricular collapse by suction. In addition, the increase in flow rate lessens as pump speed is increased, so that the derivative of the flow rate with respect to speed can indicate the need to reduce the pump speed. Moreover, the second harmonic of the current fluctuation increases just before ventricular collapse, so that the harmonic may be monitored to help indicate an appropriate pump speed. Also, the opening and closing of the aortic and mitral valves may be monitored, either with implanted microphones/hydrophones or by measuring the pulsatility of the motor current, to indicate the onset of ventricular collapse.

As indicated, there is a need for apparatuses or methods that reliably control the speed of an implantable blood pump. In particular, there is a need to provide such control to avoid left ventricular collapse over a range of blood demand by a patient.

SUMMARY

In general, a blood pump control system and method monitor the flow of blood through a blood pump and adjust the pump speed to maintain an appropriate level of assistance to the heart. A pulsatility index may be calculated, and its value may be used to determine whether a suction event in the left ventricle is imminent or is occurring. If a suction event is detected, a timer may be set and further monitoring may occur. If another suction event is detected before the timer expires, a pulsatility setpoint may be incremented so as to decrease the pump speed. If no suction event is detected for a sufficient time period, the pulsatility setpoint may be decremented so as to increase the pump speed, up to a maximum value.

In one embodiment, a method of controlling the speed of an implantable blood pump comprises monitoring a blood flow flowrate through the pump, calculating a pulsatility index for the blood flow over a control interval, modifying a pulsatility index set point if the pulsatility index indicates that ventricular collapse is imminent or occurring, and modifying the pump speed to maintain a pulsatility index substantially equal to the pulsatility index setpoint. The pulsatility index may be calculated as the percentage difference between the minimum and maximum flowrates over the control interval, and the flow rate may be monitored by measuring the blood pump motor current. The pulsatility index setpoint may be increased if the pulsatility index indicates that ventricular collapse is imminent or occurring, and may be decreased if it does not. The set point may be decreased only of a delay interval has elapsed, and the delay interval may comprise, or be equal to, a target adjustment interval that is a function of the difference between the pump speed when the imminence or occurrence of ventricular collapse, and a predetermined safe speed.

The method may also comprise calculating a plurality of pulsatility indices over a plurality of control intervals and a running average of the plurality of pulsatility indices, and determining that ventricular collapse is imminent or occurring when the percent difference between the running average and the current pulsatility index exceeds a predetermined level, such as 40–60%.

In another embodiment, a variable speed blood pump system may comprise a blood pump having a variable blood pump speed, and a blood pump volume flow sensing system to measure the volumetric flow rate of blood through the blood pump. A pulsatility setpoint controller may establish a pulsatility setpoint for the blood pump and modify the setpoint in response to changes in volumetric flowrate that signify the onset or imminence of a ventricular collapse. A pump speed controller may be responsive to the flow sensing system and adjust the blood pump speed to maintain a pulsatility index at a level approximately the same as the pulsatility setpoint. The pump speed controller may also be adapted to reduce the pump speed when the sensing system detects a flow rate that indicates the onset or imminence of ventricular collapse. In addition, a target adjustment interval timer may be provided for implementing a timer interval, wherein the pulsatility setpoint controller increases the pulsatility setpoint if the onset or imminence of ventricular collapse is detected during the timer interval. A memory may be provided for storing data representing one or more pulsatility indices, and a comparator may compare a first pulsatility index to the data. In addition, the pump speed controller may be adapted to reduce the pump speed when the comparison indicates the onset or imminence of ventricular collapse. Also, the flow sensing system may comprise a current sensor for sensing a current draw of the blood pump.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
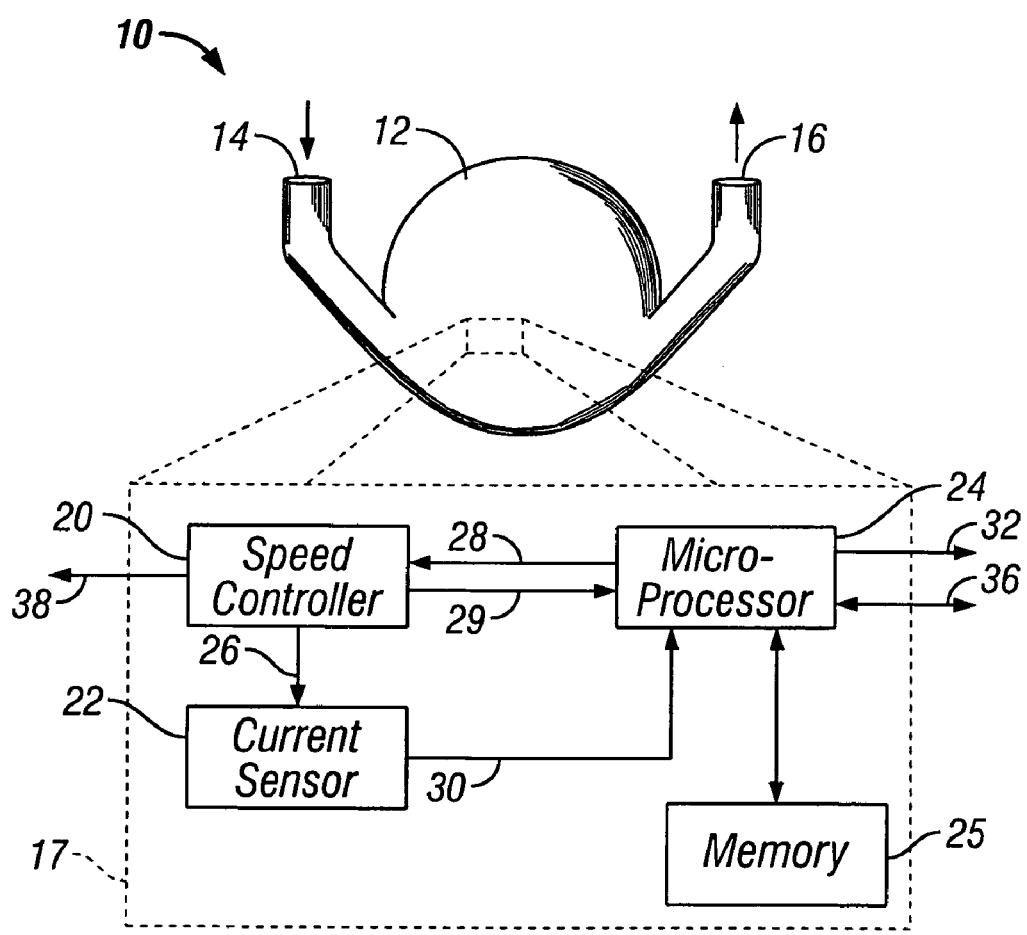
FIG. 1 shows a schematic diagram of a blood pumping system.

FIG. 1 shows a schematic diagram of a blood pumping system. The system 10 includes an implantable pump 12 in fluid communication with a patient's circulatory system. Pump 12 may be, for example, an axial flow blood pump, though other types of pumps, such as centrifugal pumps, may also be used. Pump 12 has an inlet 14 and an outlet 16. Inlet 14 may connect to a conduit (not shown) that may in turn connect to a patient's circulatory system, such as at the left ventricle. Outlet 16 may connect to another conduit (not shown) that may in turn connect to the patient's circulatory system downstream of the first conduit, such as in the aorta. Pump 12 may be implanted in a patient's abdomen or in another location proximate to the heart.

Pump system 10 may also include a pump control system 17 that may be located inside or outside pump 12. Pump control system 17 may be configured to maintain pump 12 operating at a particular speed or speeds so as to provide adequate assistance to a patient's heart. Pump control system 17 may sense the speed of pump 12 by measuring the current draw of pump 12 using current sensor 22. The speed may be sensed for each control interval, such as once per second. Pump control system 17 may maintain or change the speed of pump 12 by supplying varying current from speed controller 20 through control line 38. Speed controller 20 may be responsive to back electromotive force (BEMF) from the motor in pump 12, and may include a zero crossing detector (not shown) that detects the zero crossing of the BEMF curve. Speed controller 20 may use the BEMF and the timing of the BEMF's zero crossing to provide an appropriate level of excitation to the motor in pump 12 via motor control line 38. Other appropriate control mechanisms may also be used to control the speed of pump 12.

Microprocessor 24 may be used to establish and control an appropriate setpoint for pump 12. Microprocessor 24 may receive a signal indicative of the motor load from current sensor 22 on sensor line 30. For example, current sensor 22 may supply a signal that relates to the current drawn by the motor in pump 12, and microprocessor 24 may compute the volume of fluid flowing through pump 12 using that information. In addition, microprocessor 24 may supply a signal over command line 28 to speed controller 20 to establish a setpoint for pump 12, and may receive a signal on speed line 29 that indicates the rotational speed of pump 12. Memory 25 may also be provided for access by microprocessor 24 or other components of pump control system 17. In this manner, pump control system 17 may be a closed-loop control system in which information used to control pump 12 may be responsive to the actual operation of pump 12.

In particular, the flow through pump 12 (expressed as Q), may be calculated as a function of current draw and rotational speed, according to the following equation:

$$Q = \frac{\frac{3}{2}K_B I - B\omega - \left(a_0 \omega^3 + J\frac{d\omega}{dt}\right)}{a_1 \omega^2}$$

where J, $K_B$, B, $a_0$ and $a_1$ are all constants determined empirically for a given pump and pump motor. Microprocessor 24 may also provide alarm interface 32, which indicates the presence of an alarm condition, such as when an attempt to exceed a maximum or minimum pump speed has occurred, and diagnostics and programming interface 36, by which microprocessor 24 may report on the operation of pump 12 or may receive information to change the manner in which pump 12 is operated. Diagnostics and programming may be accomplished, for example, via a telemetric interface, and may provide a physician with an opportunity to interrogate the pump and to provide the pump with a revised operating program. Control system 17 and pump 12 may be operated by a power supply (not shown), which may include, for example, a battery that may be charged from outside the patient by induction or by other means.

Figure 2:
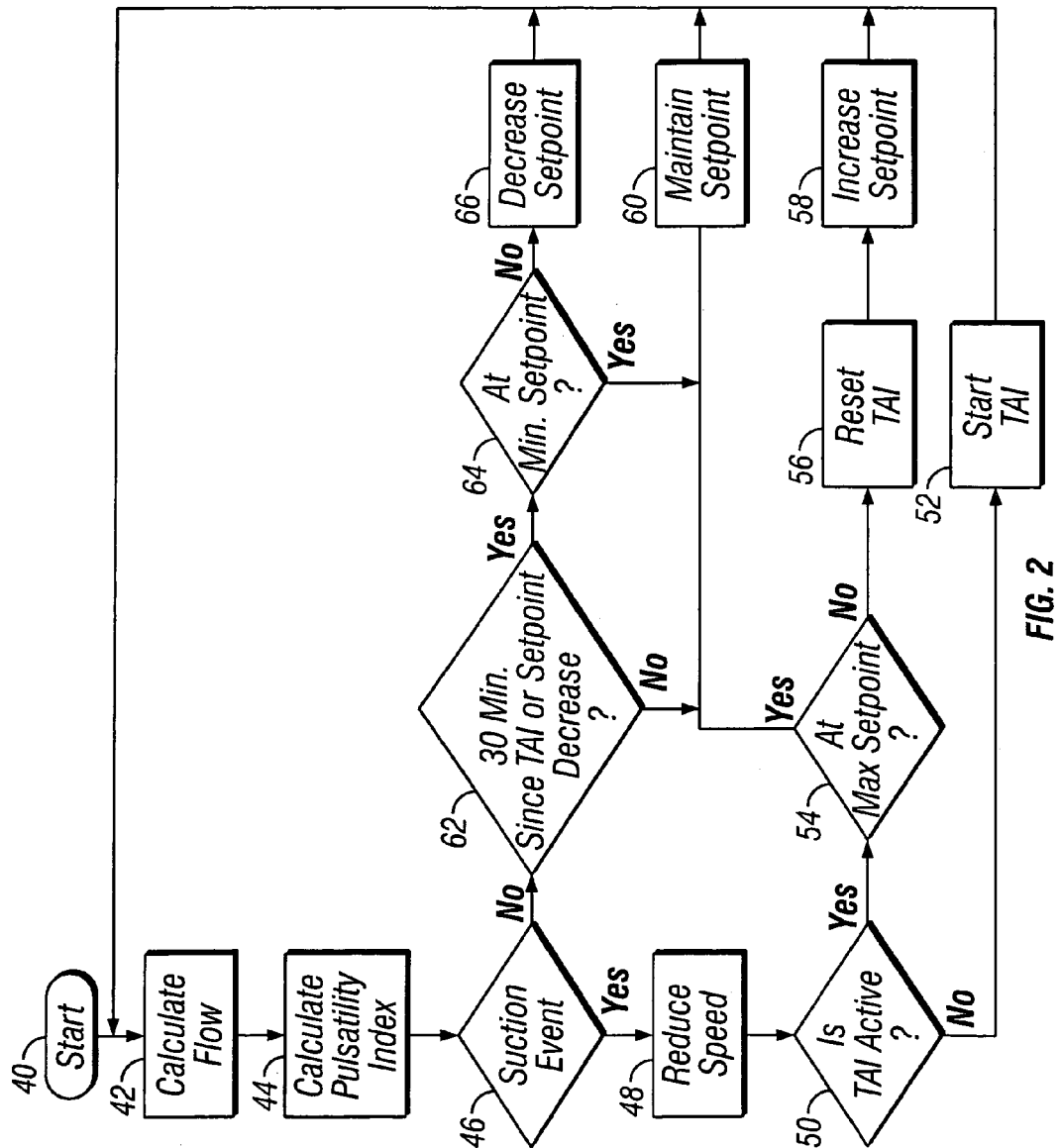
FIG. 2 illustrates a flow chart of a process for calculating a pulsatility index setpoint for a blood pump.

FIG. 2 illustrates a flow chart of a process for calculating a pulsatility index setpoint for a blood pump. The pulsatility index may provide an indication of the level of assistance that is being provided by the pump to a patient's heart. The blood pump system may increase or decrease the speed of the pump so as to maintain the pulsatility index at the pulsatility index setpoint, so that as the demand for blood by the patient increases, the speed of the pump will increase.

In general, the process calculates the blood flow through the pump on a substantially continuous basis, and uses that flow to compute a pulsatility index. If the pulsatility index differs substantially from previous pulsatility indices, the process senses a ventricular suction event, and thereby determine that the onset of ventricular collapse is occurring or is imminent. The process then slows the pump and increases the setpoint for the pulsatility index (which causes the subsequent operating speed of the pump to be reduced). If sufficient time has passed since the last suction event was sensed, the process decreases the setpoint for the pulsatility index (which causes the subsequent operating speed of the pump to be increased).

Starting at step 40, the process begins monitoring the flow through the blood pump. Flow may be calculated at block 42, for instance, by monitoring the current draw and rotational speed of the motor, as discussed above. Other means for measuring the flow, such as volumetric or mass flow sensors, could also be used. The flow rate may be sampled substantially continuously, and particular measured flow rates over time may be stored in a buffer or another form of memory. At box 44, the pulsatility index for the flow may be calculated. The pulsatility index provides a measure of the magnitude of difference between the maximum flow and the minimum flow through the pump during a time period. For example, the pulsatility index may be a dimensionless number calculated according to the following equation: $PI=(Q_{max}-Q_{min})/Q_{ave}$, where $Q_{max}$ is a maximum flowrate through the pump in the period, $Q_{min}$ is a minimum flowrate through the pump in the period, and $Q_{ave}$ is an average flowrate through the pump over the period. $Q_{ave}$ may be calculated, for example, as the midpoint between $Q_{max}$ and $Q_{min}$, or as the average of all of the volumes measured during the time period of interest.

The pulsatility index provides a measure of the level of assistance that the pump is providing to the heart. In particular, the flow of blood from the heart is irregular, while assistance provided by the pump is continuous. Thus, the blood flow through the pump will have greater variation, and higher pulsatility, when the left ventricle is pumping strongly (in comparison to the pump) because the pump will be facing relatively higher pressure differences at its input. When the pump is handling more of the load, in contrast, the blood flow will be more constant, and the pulsatility will be less, i.e., the pulsatility index will be lower.

The speed of the pump may be adjusted each time the pulsatility index is measured so as to match the pulsatility index to a pulsatility index setpoint. For example, the pump speed may be increased by a set amount, such as 100 rpm, if the measured pulsatility index is greater than the pulsatility index setpoint. Alternatively, the pump speed may be decreased by a set amount if the measured pulsatility index is less than the pulsatility index setpoint. Because higher than desired pump speeds may result in a suction event, however, the decrease in speed may be relatively greater, such as 200 rpm, so as to more quickly move to the desired speed.

The pulsatility index setpoint may be selected initially as a predetermined value, and may be adjusted over time as changes in the physiological condition of the patient's heart are sensed, as described below. In particular, the setpoint may be adjusted so that the blood pump provides sufficient assistance to the heart, but does not provide so much assistance so as to create a left ventricular collapse. By example, a clinically useful range for the pulsatility index setpoint is between approximately 0.3 and 1.0, with a setpoint between 0.6 and 0.7 being common.

The time period, or control interval, over which the pulsatility index is measured may be any appropriate period. For example, the pulsatility index may be calculated each second. As such, the flow over the time period would include approximately one to two heartbeat cycles. The time period could also be varied, for example, with the speed of the heartbeat.

A record of previous pulsatility indices may also be maintained and stored. For example, a running average of previously calculated pulsatility indices, such as those for the previous fifteen time periods, may be stored. The likely imminent onset or occurrence of ventricular suction may then be sensed, as shown at box 46, by comparing the pulsatility index of the current time period with the running average of the pulsatility indices.

If the index for the current period is sufficiently lower than the running average, the process may infer that the amount that the left ventricle is contributing to the blood flow has fallen suddenly, and that a suction event is therefore occurring or imminent. The percentage difference may be calculated, for example, by the following equation: $(PI-PI_{ave})/PI_{ave}$, where PI is the pulsatility index calculated for the present control interval, and $PI_{ave}$ is the running average of previous pulsatility indices. A suction event may be inferred, for example, when the percent difference is greater than approximately forty percent or fifty percent.

If a suction event is sensed, the process may conclude that the present speed of the blood pump is excessive, and the pump speed may be immediately reduced to prevent the continuation of the event and to restore positive pressure in the ventricle, as shown by box 48. For example, the pump speed may be reduced to a predetermined minimum safe speed, such as 9000 revolutions per minute (rpm). The pump speed may then be allowed to return to a speed required to match the measured pulsatility index to the pulsatility index setpoint. The return may proceed gradually, for example, at 100 rpm for each measured time period, as discussed above. The speed may again be reduced, however, if another suction event is detected, whether that occurs before or after the speed returns to a level that is needed to match the measured pulsatility index to the pulsatility index setpoint.

A timer for a weighted target adjustment interval (TAI) may also be started, if such a timer is not currently running, as indicated by boxes 50 and 52. The TAI may be used to differentiate between transient suction events and those suction events that are created by genuine decreases in ventricular filling. In particular, the first sensed suction event does not result in a change in the setpoint for the pulsatility index. However, if another suction event occurs during the TAI, the pulsatility index setpoint may be increased, such as by a value of 0.1 or another appropriate value. Also, the amount that the setpoint is increased may vary, and may be less as the setpoint rises. In this manner, the TAI allows for corrections in the pulsatility index setpoint to prevent continued operation of the pump at a speed that is not currently acceptable for the patient's heart.

The duration of the TAI may be calculated so as to provide a time period over which the setpoint of the pulsatility index may be incremented if a suction event is detected. As an example, the TAI may be calculated according to the following equation:

$$TAI=((Speed_{Suction}-Speed_{Safe})/\text{change rate})\times \text{delay}$$

where $Speed_{Suction}$ is the rotational speed (for example, in rpm) of the pump at the time that suction was sensed; $Speed_{Safe}$ is the speed to which the pump is reduced after a suction event is detected, as described above; change rate is the rate, in rpm/sec, at which the pump speed is approaching the setpoint speed, which is the speed at which the pump was operating when it encountered its previous suction event;

and delay is an adjustable threshold setting, that may be selected by a user or computed by the process so as to allow a quick response by the pump without over damping of the response. For example, a delay in the range of two to twenty may be appropriate.

If a TAI is already in progress when a suction event is sensed, as determined at box 50, the current pulsatility index setpoint may be compared to a value of a maximum setpoint (box 54), such as a setpoint programmed into the control system, and the setpoint may be maintained if it is currently equal to or greater than the maximum setpoint. If the current setpoint is less than the maximum setpoint, the setpoint may be increased, for example by 0.1 (box 58), and a new TAI may be calculated and started to replace the former TAI (box 56).

If a suction event has not occurred for a sufficient time period, which may be referenced as a delay interval, the pulsatility index setpoint may be decreased so as to increase the pump speed. For example, if thirty minutes have passed since the last TAI has expired, or since the pulsatility index setpoint was last decreased (box 62), the setpoint may be decreased, for example by 0.1 (box 66), and the thirty minute timer may be reset. If the setpoint is already equal to a minimum setpoint (box 64), which may be a value that is preset by the user or physician, the setpoint may be maintained at its current value (box 60). In this manner, the control system may track changes in the patient's physiology, and may incrementally increase the support provided by the blood pump over time until a suction event is detected.

Figure 3:
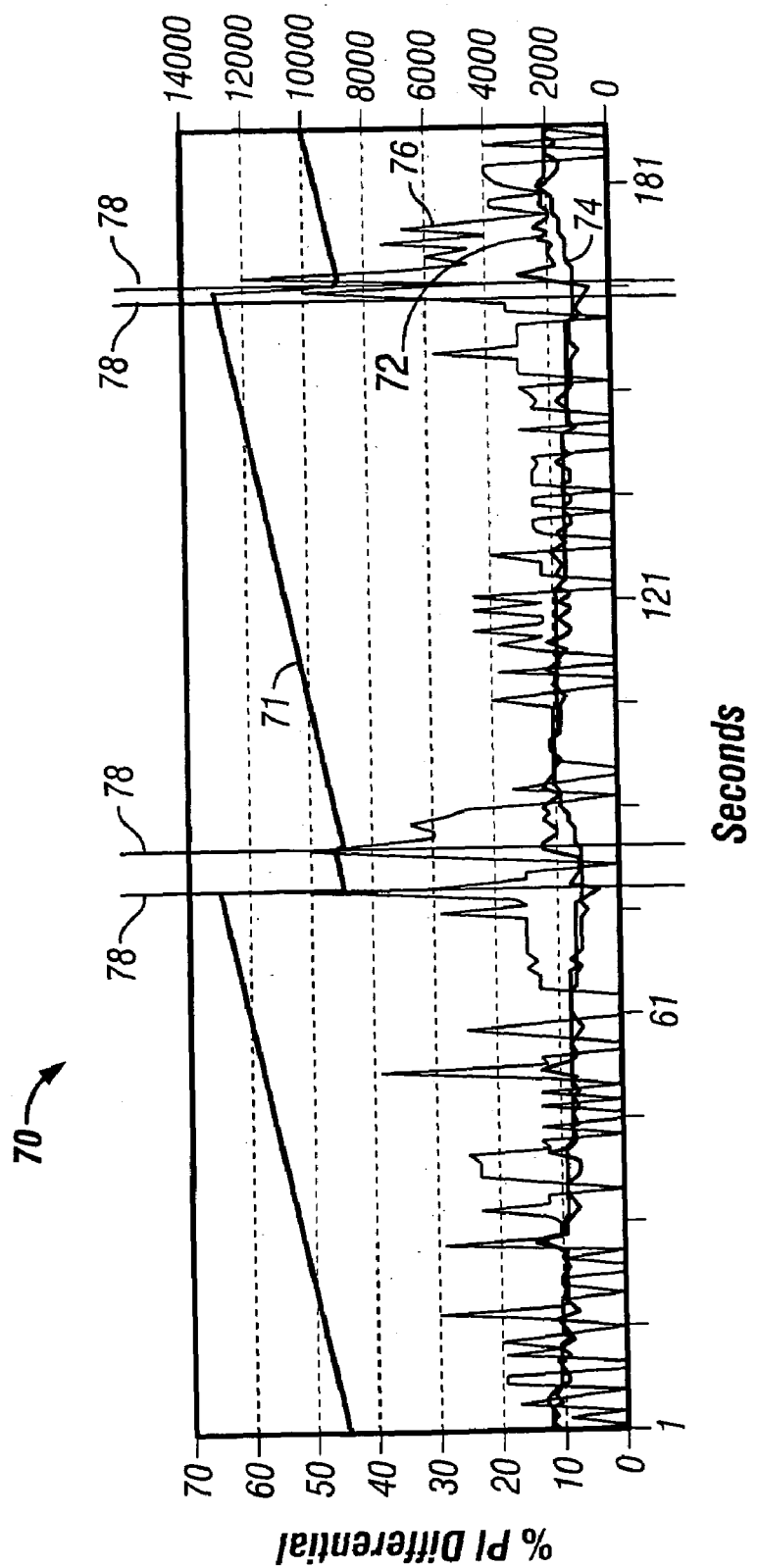
FIG. 3 shows a graph of a blood pump's pulsatility index and pump speed over time.

FIG. 3 shows a graph 70 of a blood pump's pulsatility index and pump speed over time for simulated conditions. The rotational speed of the pump in revolutions per minute is shown by line 71 and measure by the right-hand vertical axis. The pulsatility index is shown by line 72, and represents the pulsatility index that is computed for each individual control interval. The running average of pulsatility indices is shown by line 74, and represents the average of a number of previous pulsatility indices that preceded the pulsatility index that is currently being computed. The percent different between the computed pulsatility index and the running average of pulsatility indices is shown by line 76, and measured by the left-hand vertical axis. Lines 78 mark the times at which suction events are detected.

The graph shows only response to the detection of a suction event, and does not show that pump speed is being controlled to match a pulsatility index setpoint. As a result, the pump represented by the graph does not reach steady-state operation at any point before detecting a suction event. In addition, the pulsatility index setpoint is not modified when suction events are detected. Furthermore, the control interval in the example is two seconds, so that the pump speed is increased at fifty rpm per second. In addition, the pulsatility index that is deemed to indicate a suction event is forty percent in the graph.

In operation, the pump begins operating at an assumed safe speed of 9000 rpm. The speed of the pump is increased steadily until a suction event is sensed at about eighty seconds, when the percent difference between the measured pulsatility index and the running average of pulsatility indices exceeds forty percent. As shown by line 76, the percent difference between the measured pulsatility index and the average of the pulsatility indices does not exceed forty percent during the initial eighty seconds, so no suction event is detected by the process, and the pump speed is allowed to increase. When the suction event is detected, however, the speed is dropped to 9000 rpm, and then begins to increase again. At approximately eighty-five seconds, the percent difference again exceeds forty percent, and the speed is again dropped to 9000 rpm. The cycle of increasing the pump speed then begins again, until two suction events are again detected at approximately one-hundred-sixty-five seconds. Thus, in this manner, the pump speed can be reduced when a suction event is sensed, assumed to be indicative of ongoing or imminent ventricular collapse, and may subsequently be increased so that the pump provides more than minimal support to the heart.

Advantageously, the process just described allows a blood pump to adjust its support as the physiological conditions of the patient change, by maintaining a particular pulsatility index. In addition, the process allows the system to maximize the level of support provided without creating ventricular collapse, by monitoring the blood flow for suction events, increasing the setpoint for the pulsatility index (and thereby decreasing pump speed) if a suction event is detected or sensed, and decreasing the setpoint for the pulsatility index (and thereby increasing pump speed) if no suction event is sensed for a sufficient time period.

Other formulations for the pulsatility index may also be used to measure the conditions of the blood pump and to establish an operating setpoint. For example, the derivative of flow volume with respect to speed may also be used as a setpoint. The setpoint for the derivative value may be increased incrementally as a suction event is detected, so as to effect a lower operating speed for the pump.

For example, the pump may begin operation at a particular speed, and the speed may be increased by a set amount for each control interval, such as by one-hundred rpm each second, or some other value that has been determined to provide a usable increase in flow during normal operation. After each increase in speed, the flow before the increase may be compared to the flow after the increase. If the increase in flow is greater than a predetermined value or percentage, the speed may again be increased and the measurements repeated. If the increase in flow is less than a predetermined value or percentage, the process may enter a dither mode, by which the speed is reduced by a set amount for each control interval, such as by two-hundred rpm each second. Once the flow rate has stabilized during the dither period, the process may again start increasing the pump speed by a set amount, and the cycle may be repeated continuously. If a suction event is detected, a TAI period may be started as discussed above, and the predetermined percentage that causes a reduction in speed may be increased so that the pump speed is less likely to enter the speed range at which suction is likely to occur.

It should be understood that various modifications could be made without departing from the spirit and scope of the invention. In particular, the invention is intended to be operable in any of a number of environments, and using any of a number of arrangements of elements. For example, various numbers, types, and arrangements of structures may be provided to compute the flow through a blood pump and to adjust the pump speed. In addition, the degree of assistance provided by the pump may be sensed in any of a number of ways, and the pump speed may be adjusted by any of a number of processes. Accordingly, other implementations are within the scope and coverage of the following claims.

What is claimed is:

1. A method of controlling the speed of an implantable blood pump, comprising:
   monitoring a blood flow flowrate through the pump;
   calculating a pulsatility index for the blood flow over a control interval;

modifying a pulsatility index set point if the pulsatility index indicates that ventricular collapse is imminent or occurring; and modifying the pump speed to maintain a pulsatility index substantially equal to the pulsatility index setpoint.

2. The method of claim 1, wherein the pulsatility index (PI) is calculated over a control interval according to the following equation: PI=(Qmax−Qmin)/Qave, where Qmax is a maximum flowrate through the pump in the control interval, Qmin is a minimum flowrate through the pump in the control interval, and Qave is an average flowrate through the pump over the control interval.

3. The method of claim 1, wherein the blood flow flowrate is monitored by measuring the motor current for the blood pump motor.

4. The method of claim 1, wherein the pulsatility index set point is increased if the pulsatility index indicates that ventricular collapse is imminent or occurring.

5. The method of claim 4, further comprising decreasing the pulsatility index set point if the pulsatility index indicates that ventricular collapse is not imminent or occurring.

6. The method of claim 5, wherein the pulsatility index set point is decreased only if a delay interval has elapsed since the imminence or occurrence of ventricular collapse has been determined.

7. The method of claim 6, wherein the delay interval comprises a target adjustment interval (TAI) that is a function of the difference between the pump speed when the imminence or occurrence of ventricular collapse was determined, and a predetermined safe pump speed.

8. The method of claim 7, wherein the TAI is calculated by the following equation:

TAI=((SpeedSuction−SpeedSafe)/change rate)×delay,

Where SpeedSuction is the pump speed when the imminence or occurrence of ventricular collapse was determined, SpeedSafe is a predetermined safe pump speed, change rate is the rate of change in pump speed over a predetermined control interval, and delay is a predetermined amount.

9. The method of claim 7, wherein the delay interval is equal to the TAI.

10. The method of claim 1, further comprising:

calculating a plurality of pulsatility indices over a plurality of control intervals, calculating a running average of the plurality of pulsatility indices; and determining that ventricular collapse is imminent or occurring when the percent difference between the pulsatility index for the control interval and the running average exceeds a predetermined level.

11. The method of claim 10, wherein the predetermined level is between 40 percent and 60 percent.

12. A variable speed blood pump system, comprising:

a blood pump having a variable blood pump speed;

a blood pump flow sensing system to measure the flow rate of blood through the blood pump;

a pulsatility setpoint controller that establishes a pulsatility setpoint for the blood pump, and modifies the pulsatility setpoint in response to changes in volumetric flowrate through the pump that signify the onset or imminence of a ventricular collapse; and a pump speed controller responsive to the blood pump volume flow sensing system that adjusts the blood pump speed to maintain a pulsatility index at a level approximately the same as the pulsatility setpoint.

13. The system of claim 12, wherein the pump speed controller is adapted to reduce the blood pump speed when the blood pump flow sensing system detects a flow rate that indicates the onset or imminence of a ventricular collapse.

14. The system of claim 13, further comprising a target adjustment interval tinier for implementing a timer interval, and wherein the pulsatility setpoint controller increases the pulsatility setpoint if the onset or imminence of ventricular collapse is detected during the timer interval.

15. The system of claim 12, further comprising a memory for storing data representing one or more pulsatility indices, and a comparator for comparing a first pulsatility index to the data representing one or more pulsatility indices.

16. The system of claim 15, wherein the pump speed controller is adapted to reduce the blood pump speed when the comparison between the first pulsatility index and the data representing the one or more pulsatility indices indicates the onset or imminence of ventricular collapse.

17. The system of claim 12, wherein the blood pump flow sensing system comprises a current sensor for sensing a current draw of the blood pump.

\* \* \* \* \*

UNITED STATES PATENT AND TRADEMARK OFFICE
CERTIFICATE OF CORRECTION

| | | |
|---|---|---|
| PATENT NO. | : 6,991,595 B2 | Page 1 of 1 |
| APPLICATION NO. | : 10/125943 | |
| DATED | : January 31, 2006 | |
| INVENTOR(S) | : David J. Burke and Douglas C. Thomas | |

It is certified that error appears in the above-identified patent and that said Letters Patent is hereby corrected as shown below:

Column 10, line 27, please delete "tinier" and insert --timer--therefor.

Signed and Sealed this

Eighteenth Day of July, 2006

JON W. DUDAS
*Director of the United States Patent and Trademark Office*